US011439797B2

(12) United States Patent
Guirguis et al.

(10) Patent No.: US 11,439,797 B2
(45) Date of Patent: Sep. 13, 2022

(54) SURGICAL DRAIN SYSTEM AND CONTAINER

(71) Applicant: MEDTRONIC ADVANCED ENERGY LLC., Minneapolis, MN (US)

(72) Inventors: Mark Guirguis, Minneapolis, MN (US); Nathan Zamarripa, Minneapolis, MN (US); Nicholas Valley, Minneapolis, MN (US); Christian Schasel, Minneapolis, MN (US)

(73) Assignee: MEDTRONIC ADVANCED ENERGY LLC., Minneapolis, MN (US)

( * ) Notice: Subject to any disclaimer, the term of this patent is extended or adjusted under 35 U.S.C. 154(b) by 376 days.

(21) Appl. No.: 15/879,034

(22) Filed: Jan. 24, 2018

(65) Prior Publication Data
US 2018/0229014 A1 Aug. 16, 2018

Related U.S. Application Data

(60) Provisional application No. 62/457,473, filed on Feb. 10, 2017.

(51) Int. Cl.
*A61M 27/00* (2006.01)
*A61M 1/00* (2006.01)
*A61F 5/44* (2006.01)

(52) U.S. Cl.
CPC .......... *A61M 27/00* (2013.01); *A61M 1/0001* (2013.01); *A61M 1/0003* (2013.01);
(Continued)

(58) Field of Classification Search
CPC .. A61M 1/0025; A61M 27/00; A61M 1/0001; A61M 1/0003; A61M 1/0086;
(Continued)

(56) References Cited

U.S. PATENT DOCUMENTS 3,952,727 A 4/1976 Nolan
4,930,997 A * 6/1990 Bennett ............... A61M 1/0023
417/410.1
(Continued)

FOREIGN PATENT DOCUMENTS

AU 2014200853 3/2014
EP 2781166 B1 9/2015
(Continued)

OTHER PUBLICATIONS

U.S. Appl. No. 62/409,400, filed Oct. 18, 2016; "Portable Device with Disposable Reservoir for Collection of Internal Fluid After Surgery"; First named inventor: Joshua Herwig.
(Continued)

*Primary Examiner* — Tatyana Zalukaeva
*Assistant Examiner* — Meagan Ngo
(74) *Attorney, Agent, or Firm* — Dicke, Billig & Czaja, PLLC

(57) ABSTRACT

A container for a portable surgical drain system to receive a fluid from a drain at a surgical site is disclosed. The container includes a drain hub having at least one sensor and a cartridge removably coupled to the drain hub in fluid communication with the drain to provide a suction source to draw and receive the fluid from the surgical site. The at least one sensor detects a characteristic of the fluid in the cartridge.

56 Claims, 4 Drawing Sheets

(52) U.S. Cl.
CPC ............ *A61M 1/0023* (2013.01); *A61M 1/73* (2021.05); *A61M 1/80* (2021.05); *A61M 1/86* (2021.05); *A61F 5/4404* (2013.01); *A61M 2205/103* (2013.01); *A61M 2205/12* (2013.01); *A61M 2205/18* (2013.01); *A61M 2205/215* (2013.01); *A61M 2205/3306* (2013.01); *A61M 2205/3379* (2013.01); *A61M 2205/3553* (2013.01); *A61M 2205/3561* (2013.01); *A61M 2205/3592* (2013.01); *A61M 2205/8206* (2013.01); *A61M 2209/088* (2013.01)

(58) Field of Classification Search
CPC .............. A61M 1/0066; A61M 1/0023; A61M 2205/12; A61M 2209/088; A61M 2205/8206; A61M 2205/3553; A61M 2205/3306; A61M 2205/215; A61M 2205/3592; A61M 2205/103; A61M 2205/18; A61M 2205/3379; A61M 2205/3561; A61M 1/005; A61M 1/0082; A61M 1/73; A61M 1/60; A61M 1/95; A61F 5/4404; A61B 2562/168; A61B 2562/18; A61B 2562/00; G01F 17/00; G01N 27/4078
See application file for complete search history.

(56) References Cited

U.S. PATENT DOCUMENTS

| | | | |
|---|---|---|---|
| 5,944,703 | A | 8/1999 | Dixon et al. |
| 6,010,453 | A | 1/2000 | Fiddian-Green |
| 6,695,825 | B2 | 2/2004 | Castles |
| 7,267,671 | B2 | 9/2007 | Shehada |
| 7,322,971 | B2 | 1/2008 | Shehada |
| 8,696,403 | B2 | 4/2014 | Haley |
| 8,911,765 | B2 | 12/2014 | Moses et al. |
| 9,457,129 | B2 | 10/2016 | Buevich et al. |
| 10,532,135 | B2 | 1/2020 | Lopez et al. |
| 10,549,016 | B2 | 2/2020 | Bushko et al. |
| 10,744,239 | B2 | 8/2020 | Armstrong et al. |
| 2004/0000349 | A1 | 1/2004 | Cull et al. |
| 2004/0116902 | A1* | 6/2004 | Grossman ............ A61M 1/0027 604/540 |
| 2006/0074484 | A1 | 4/2006 | Huber |
| 2007/0167927 | A1 | 7/2007 | Hunt et al. |
| 2008/0168836 | A1 | 7/2008 | Wu et al. |
| 2009/0012493 | A1* | 1/2009 | Harig ................. A61M 1/0003 604/404 |
| 2009/0293887 | A1 | 12/2009 | Wilkes et al. |
| 2010/0049150 | A1* | 2/2010 | Braga ................. A61M 1/0049 604/313 |
| 2010/0198175 | A1* | 8/2010 | Rosero .................... A61M 1/82 604/320 |
| 2010/0204765 | A1 | 8/2010 | Hall et al. |
| 2011/0130712 | A1 | 6/2011 | Topaz |
| 2012/0136325 | A1 | 5/2012 | Allen et al. |
| 2012/0208285 | A1* | 8/2012 | Deighan ................ A61B 5/061 436/163 |
| 2012/0302938 | A1* | 11/2012 | Browd ................ A61M 27/006 604/9 |
| 2012/0316491 | A1 | 12/2012 | Joensson |
| 2013/0267918 | A1* | 10/2013 | Pan ..................... A61M 1/0088 604/318 |
| 2013/0327326 | A1 | 12/2013 | Brennan |
| 2013/0331805 | A1* | 12/2013 | Brennan ............ A61M 1/0001 604/321 |
| 2014/0194840 | A1* | 7/2014 | Eckermann ......... A61M 1/0025 604/328 |
| 2014/0350494 | A1 | 11/2014 | Hartwell et al. |
| 2015/0019257 | A1* | 1/2015 | Doyle .................... G16H 50/20 705/3 |
| 2015/0025485 | A1* | 1/2015 | Luckemeyer ....... G01F 23/2967 604/319 |
| 2015/0359457 | A1 | 12/2015 | Blumenthal et al. |
| 2016/0082165 | A1 | 3/2016 | Alvarez et al. |
| 2016/0256615 | A1 | 9/2016 | Poormand |
| 2017/0021128 | A1 | 1/2017 | Erbey, II et al. |
| 2017/0095648 | A1 | 4/2017 | Nowak |
| 2017/0100068 | A1 | 4/2017 | Kostov |
| 2017/0112981 | A1* | 4/2017 | Friedman .............. A61M 39/28 |
| 2017/0128639 | A1* | 5/2017 | Erbey, II .......... A61M 25/0026 |
| 2017/0196478 | A1 | 7/2017 | Hunter |
| 2017/0197018 | A1* | 7/2017 | Mukherjee .......... A61M 1/0031 |
| 2017/0281064 | A1* | 10/2017 | Bayon ................ A61B 5/14539 |
| 2018/0000999 | A1 | 1/2018 | Dolmatch et al. |
| 2018/0228945 | A1 | 8/2018 | Guirguis et al. |
| 2018/0296737 | A1 | 10/2018 | Sivakumaran et al. |
| 2019/0151515 | A1* | 5/2019 | Selby ................... A61M 1/734 |
| 2020/0000979 | A1 | 1/2020 | Myers |

FOREIGN PATENT DOCUMENTS

| | | |
|---|---|---|
| WO | 2014160481 | 10/2014 |
| WO | 2017148824 A1 | 9/2017 |
| WO | 2017205446 A1 | 11/2017 |

OTHER PUBLICATIONS

U.S. Appl. No. 62/340,853, filed May 24, 2016; "Portable Device with Disposable Reservoir for Collection of Internal Fluid after Surgery"; First named inventor: Esra Roan.

Chevrollier G.S., Rosato F.E., Rosato E.L. (2018) Fundamentals of Drain Management In: Plazzo F. (eds) Fundamentals of General Sugery. Springer, Cham https://doi.org/10.1007/978-3-319-75656-1_11 (Year: 2018).

Definition of Lubricious (Year: 2021).

Regtien, Paul and Edwin Dertien, "Sensors for Mechanics, second edition: Chapter 7: Optical sensors" pp. 183-243 (hereafter referred to as Regtien and chapter number) (Year: 2018).

* cited by examiner

SURGICAL DRAIN SYSTEM AND CONTAINER

CROSS REFERENCE TO RELATED APPLICATION

This Non-Provisional Utility Application claims benefit to U.S. Provisional Application No. 62/457,473, filed Feb. 10, 2017, titled "SURGICAL DRAIN SYSTEM," the entirety of which incorporated herein by reference.

BACKGROUND

This disclosure relates generally to the field of medical devices, systems and methods for use in surgical recovery after surgical procedures or medical treatment. More specifically, this disclosure relates to a portable surgical drain system having a portable container in fluid communication with an implantable drain, in which the portable container includes at least one sensor and a processing circuit.

A surgical drain is a medical device that may be used after surgery to remove accumulated bodily fluids such as pus, blood, or other fluids and small solids such as fibrin, clot, or other materials from a wound or surgical site. In one example, a surgical drain can be a portable medical device that includes an internal drain coupled to a fluid-collection container via tubing. Examples of portable drains can be active drains or passive drains of various sizes. Active drains can be attached to a suction source, such as closed-suction drains. Passive drains have no suction source and work according to the differential pressure between the body cavity and the exterior.

A Jackson-Pratt drain is one example of a closed-suction portable medical device that is commonly used as post-operative drain for collecting bodily fluids from closed spaces that may cause either disruption of the wound and healing process or become an infected abscess. Either scenario may require a formal drainage or repair procedure and possibly another visit to the operating room. Portable closed-suction drains can be applied to various surgical sites such as abdominal surgery, breast surgery including mastectomies, thoracic surgery, joint replacements, and craniotomies. Additionally, such drains can be used to evacuate an internal abscess before surgery when an infection already exists.

A closed suction can be provided with a flexible grenade-shaped bulb fluid-collection container. The patient, caregiver, or healthcare provider can squeeze the air out of an empty bulb and attach the tubing to the surgical drain before releasing the bulb. The resulting vacuum creates suction in the tubing and drain, which gradually draws fluid from the surgical site into the bulb. The bulb may be repeatedly reopened to remove the collected fluid and squeezed to restore suction.

Typically, the patient or caregiver is tasked with examining the fluid for signs of possible infection or blood and to accurately measure and record the drainage output. Handling of the drain system is a potential source of infection, and a requirement of self-monitoring the fluid is susceptible to patient or caregiver error or inaccuracies, which can lead to complications and ineffective treatment.

Drain systems, such as Jackson-Pratt drains, have a tendency to become clogged or occluded with fibrin, clot, or other material. This results in loss of drain patency and thus fluid, blood or infected material can build up in the wound resulting in a wound hematoma, abscess, infection, or other complication. The patient or caregiver is also tasked to make sure the drains do not clot or become clogged when they are still in use. This risk can be reduced by a daily subcutaneous injection of low-molecular-weight heparin until the surgical drain is removed. Once a drain becomes clogged or occluded, it is usually stripped by hand to remove the clog. The drain system may be removed if stripping is unsuccessful, as it no longer provides any benefit.

SUMMARY

This summary is provided to introduce a selection of concepts in a simplified form that are further described below in the Detailed Description.

In one aspect, the disclosure is directed to a portable drain system having a drain in fluid communication with a container. The drain is configured to drain fluid from a wound or surgical site and the container collects the fluid. In one example, the drain is a subdermal drain implantable in a patient's body and the container is worn on the outside of the body. The drain system includes sensors to detect one or more of fluid color, fluid volume, and orientation of the container. The one or more sensors can be provided to a processing circuit that can include a processor. Volume of the drainage fluid can be detected at multiple times to determine an amount of fluid flow with the processor. In one example, the processor can detect sensor signals representative of drainage fluid volume at times that the container is in a selected orientation, such as upright. In one example, the one or more sensors and processing circuit are located on the container.

In another aspect, the disclosure is directed to a portable drain system having a clog remover system. In one example, the one or more sensors can be applied to detect clogs in a lumen from the drain to the container. For instance, the processing circuit can inferentially determine a clog is present if fluid volume has not changed or has not changed an expected amount over a selected period of time. If a clog is detected, the processing circuit can operate a clog remover for a selected amount of time to remove the clog. In one example, the clog remover includes a turbine in the lumen that will rotate about an axis to loosen and/or release the clog. In another example, the clog remover system is operated without the processing system, such as the turbine is constantly operating while the container is configured to receive fluid.

In another aspect, the disclosure is directed to a portable drain system having wireless-network communication features. For example, the processing circuit is operably coupled to a communications module on the drain system, such as on the container. The communications module is configured to transmit computer data via a wireless-network, such as wireless local area network or wireless personal network, to a computing device or network intermediary. The computing device or network intermediary is configured to transmit data related to the computer data to a remote server. In one example, the data related to the computer data on the remote server is accessible via a browser-based application. In one example, the processing circuit provides notifications to the user via the computing device and to a clinician via the remote server. For instance, the processing circuit can alert the patient's smart phone or laptop that the container is filled with fluid. In some examples, the clog remover or other features of the container or portable drain system can be operated remotely via the wireless-network communication features such as via a computer application operated by the patient or a caregiver.

In another aspect, the disclosure is directed to an active portable drain system. The container can include a drain hub and a replaceable cartridge. In one example, the drain hub includes at least one of the one or more sensors, the processing circuit, the communications module, and the clog remover. The cartridge is configured to receive the fluid in a vessel and can be replaced, such as when the cartridge is full. In one example, the cartridge is disposable. In one example, the vessel is provided with a prescribed vacuity such that a differential pressure between the surgical or wound site and vessel is established when the cartridge is inserted into the drain hub to draw fluid into the container.

In one example, the disclosure includes a container for a portable surgical drain system to receive a fluid from a drain at a surgical site. The container includes a drain hub having at least one sensor and a pumpless cartridge removably coupled to the drain hub in fluid communication with the drain to draw and receive the fluid from the surgical site. The at least one sensor detects at least one of fluid color, fluid volume in the cartridge, and orientation of the container.

In one example, the entire drain system, the container, or the cartridge can be pumpless. "Pumpless," in this disclosure means the cartridge, container, or drain system does not use a mechanical pump to move fluid along a pathway from the surgical site into the container. A mechanical pump can include a positive displacement pump such as a peristaltic pump and uses some mechanism that consumes energy to produce work that moves the fluid. For example, a pumpless cartridge, container, or drain system draws fluid via a source of negative pressure such as a prescribed vacuity instead of using a mechanical pump in the cartridge, container, or drain system.

In another example, the disclosure includes a container for a portable surgical drain system to receive a fluid from a drain at a surgical site. The container includes a drain hub having at least one sensor and a generally rigid cartridge removably coupled to the drain hub in fluid communication with the drain to draw and receive the fluid from the surgical site. The generally rigid cartridge includes a prescribed vacuity when installed into the drain hub. The at least one sensor detects a characteristic of the fluid in the cartridge.

In another example, the disclosure includes a container for a portable surgical drain system to receive a fluid from a drain at a surgical site. The container includes a drain hub having at least one sensor and a generally rigid cartridge removably coupled to the drain hub in fluid communication with the drain to provide a suction source to draw and receive the fluid from the surgical site. The at least one sensor detects a characteristic of the fluid in the cartridge.

In another example, the disclosure includes a portable container for a surgical drain system to receive a fluid from a drain at a surgical site. The container includes a drain hub in fluid communication with the drain and a cartridge removably coupled to the drain hub in fluid communication with the drain to receive the fluid from the surgical site. The drain hub includes at least one sensor to configured to detect at least one of fluid color, fluid volume in the cartridge, and orientation of the container. The drain hub includes a fluid pathway configured to be in fluid communication with the drain and the cartridge, wherein the fluid pathway includes a turbine configured to be rotated about an axis within the fluid pathway.

In another example, the disclosure includes a container for a portable surgical drain system to receive a fluid from a drain at a surgical site. The container includes a drain hub having at least one sensor and a fluid pathway configured to be in fluid communication with the drain, the fluid pathway including a turbine configured to be rotated about an axis of rotation within the fluid pathway. The container also includes a generally rigid cartridge removably coupled to the drain hub in fluid communication with the drain to draw and receive the fluid from the surgical site, the generally rigid cartridge having a prescribed vacuity when installed into the drain hub. The at least one sensor detects a characteristic of the fluid in the cartridge and the turbine rotated by a force from the prescribed vacuity of the cartridge.

In another example, the disclosure includes a portable container for a surgical drain system to receive a fluid from a drain at surgical site of a drain system. The portable container includes a sensor, a processing circuit, a communications module, and a turbine. The sensor is configured to detect fluid flow in the drain system. The processing circuit is operably coupled to the sensor and configured to receive signals from the sensor. The communications module is operably coupled to the processing circuit to transmit computer data received from the processing circuit to a computing device on over a wireless-network. The turbine is operably coupled to the processing circuit wherein the processing circuit is configured to selectively operate the turbine if a clog is determined in the drain system.

In another example, the disclosure includes a container for a portable surgical drain system to receive a fluid from a drain at a surgical site. The container includes a drain hub and a cartridge. The drain hub includes a plurality of walls and a sensor. The cartridge is removably coupled to the drain hub in fluid communication with the drain to provide a suction source to draw and receive the fluid from the surgical site. The sensor detects a characteristic of the fluid in the container and the cartridge is received within the walls of the drain hub.

In another example, the disclosure includes a container for a portable surgical drain system to receive a fluid from a drain at a surgical site. The container includes a drain hub and a cartridge. The drain hub includes a top receiver and a plurality of sides, wherein the top receiver includes a drain connection and a fluid pathway configured to be in fluid communication with the drain, and wherein at least one of the plurality of sides includes a sensor. The cartridge is removably coupled to the drain hub in fluid communication with the drain to provide a suction source to draw and receive the fluid from the surgical site. The sensor detects a characteristic of the fluid in the container and the cartridge is received within the walls of the drain hub.

DETAILED DESCRIPTION

Figure 1:
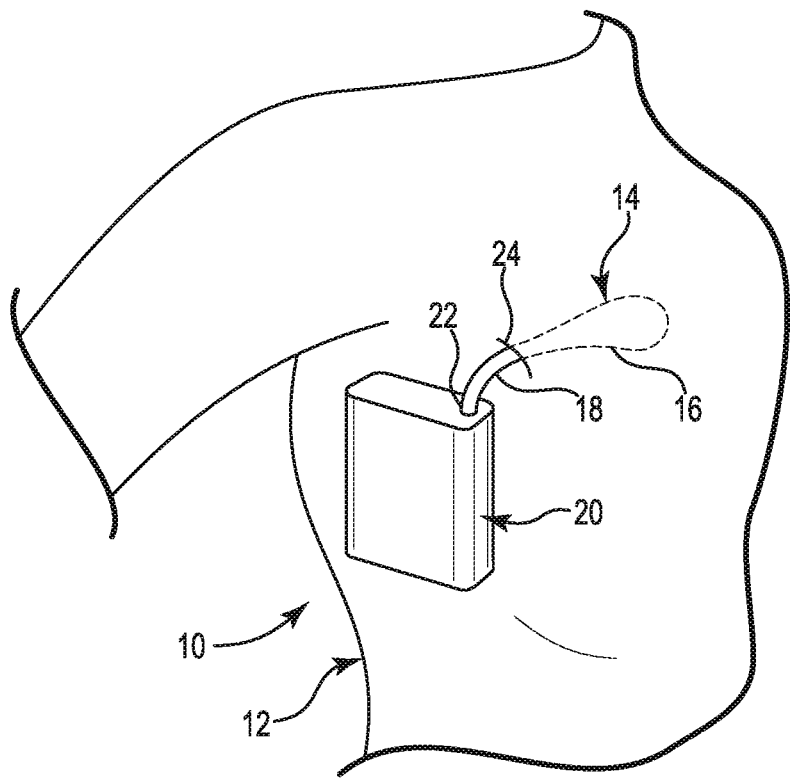
FIG. 1 is a front view of an example environment of an example drain system coupled to a patient's body.

Throughout the description, like reference numerals and letters indicate corresponding structure throughout the several views. Also, any particular features(s) of a particular exemplary embodiment may be equally applied to any other exemplary embodiment(s) of this specification as suitable. That is, features between the various exemplary embodiments described herein are interchangeable as suitable and may not be exclusive. From the specification, it should be clear that the terms "distal" and "proximal" are made in reference to a user of the device.

FIG. 1 illustrates an example environment for an example surgical drain system 10.

The surgical drain system 10 is configured to include a portion for implantation within a patient's body 12 proximate the surgical or wound site 14 of interest. In the example environment of FIG. 1, the surgical drain system 10 is implanted in the patient's torso to drain fluid resulting from a mastectomy. Other example environments and surgical sites are contemplated. In one example, the drain system 10 is portable such that it carried on the body, configured to travel with the patient, and does not generally interfere with a patient's mobility. For example, the portable drain system 10 can be worn on the body and carried from location to location, including locations away from a care facility. In one example, the portable drain system 10 can continue to communicate with clinicians at a care facility when worn in remote locations.

The drain system 10 includes an implantable drain 16, which can be selected from one or more drains particularly configured to be positioned at the surgical or wound site 14, in fluid communication with a fluid-collection container 20 via tubing 18. In one example, the tubing 18 may be integrally formed with the drain 16 and coupled to the container 20 or a separate piece that is coupled to the drain 16 and the container 20 at a distal end 22 of the tubing 18. The drain 16 and tubing 18 form a lumen such that fluid from the surgical or wound site 14 is drawn into the drain 16 and transported into the container 20 via the tubing 18 by way of an active or passive process associated with the drain system 10.

In the example of mastectomy, the drain 16 can be a standard subdermal drain positioned proximate the pectoralis major muscle at the surgical site 14. The patient's body 12 may include one or more drain incisions 24 for the tubing 18 to extend into the body 12 to the surgical site 14. The container 20 can be positioned outside of the body 14 against the torso such as proximate the under arm. More than one drain systems may be used on a patient at a time. The drain system 10 can be carried on the body via straps, a holster, brace, pockets on a general or specialized clothing article, tape, other attachment mechanism.

The drain system 10 can be constructed from materials configured to reduce the chance of irritation and other complications. The drain 16 and tubing 18 may be constructed from any material suitable for implantation with the body 12, and the material may be selected to reduce the chances of allergy or other reaction. For example, the material may be of a biocompatible silicone, polyether ether ketone (PEEK), polyvinyl chloride (PVC), polytetrafluoroethylene (PTFE), or other material. The tubing 18 may be formed from PVC, PEEK, or a thermoplastic elastomer (TPE) such as a polyether block amine (PEBA). Aspects of the drain system, such as the tubing 18 or drain 16 can include a hydrophilic or lubricious coating, for example, to assist in removal from the surgical site 14 or drain incision 24.

In the example, the container 20 includes a smooth wall design without sharp corners to cut or pinch the body 12 as well as a low profile to tuck neatly under the arm or against the body 12 to help conceal the drain system 10, fit under clothes, not restrict movement, and reduce discomfort. The container 20 may include an ergonomic design to reduce irritation and promote comfort, and it may be constructed from a synthetic polymer outer surface or have a polymer shell, coating or a removable cover such as polycarbonate, acrylonitrile-butadiene-styrene (ABS), or other material. As indicated in the example, the features of the container 20 can be incorporated into a single, unitary block or piece without attachments or accessories to promote a stable, ergonomic object.

Figure 2:
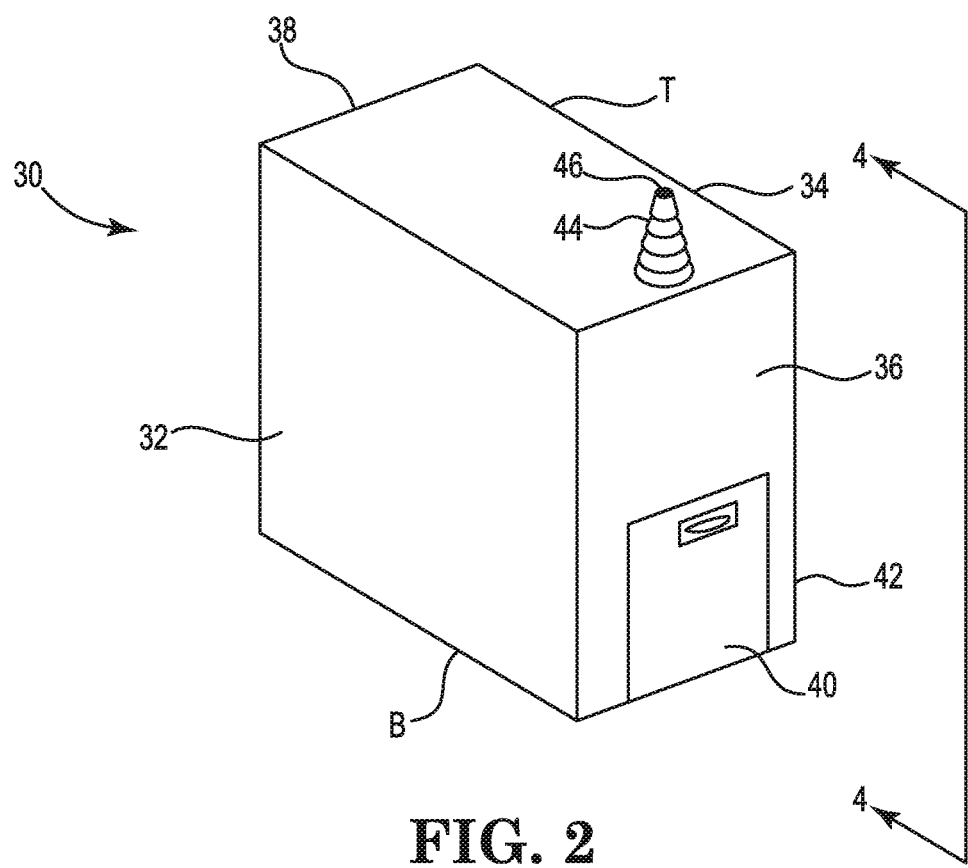
FIG. 2 is a perspective view of an example container of the drain system of FIG. 1.

FIG. 2 illustrates an example container 30, which can be an example of container 20 of drain system 10. Container 30 can include a top surface T, or side configured to be proximate the surgical site 14, and an bottom surface B opposite the top surface T, or side configured to be distal from the surgical site 14. The container 30 can also include a pair of opposing major surfaces 32, 34, wherein one of the major surfaces 32, 34 can configured to be positioned against the patient's body 12. In some examples, the major surfaces 32, 34 can be curved or formed for comfort, such as one major surface can be concave and the other convex, generally flat, or some combination of the two. The container 30 can also include a pair of opposing side surfaces 36, 38.

The container 30 includes cartridge 40 removably coupled to a drain hub 42. The drain hub 42 includes a drain connection 44 having a fluid port 46 in fluid communication with the cartridge 40. The drain connection 44 can be configured to be removably secured to the tubing 18 such that the fluid port 46 is fluidically coupled to the drain 16. In the example, the drain connection 44 can include one or more barbs to removably secure the tubing to the container 30. The fluid port 46 is fluidically coupled to a fluid pathway 48 within the drain hub 42 that is in fluid communication with the cartridge 40. Fluid received at the fluid port 46 can travel via the fluid pathway 48 into the cartridge 40 and be received into the cartridge 40. As indicated in the example, the removable cartridge 40 can be contained within or substantially within the drain hub 42. For example, the opposing major surfaces 32, 34 can extend distally to the bottom surface B of the container 30, which can be formed by the cartridge 40. The length of the bottom surface B between side surfaces 36, 38, and width of the bottom surface B major surfaces 32, 34 can be contained within or substantially within the dimensions of the opposing major surfaces 32, 34. In the illustrated example, the drain connection 44 is included on the top surface T and extending generally perpendicular from the top surface T, although other configurations or locations for the drain connection 44 are contemplated.

In the examples, the drain hub 42 can include sensors, circuitry, and a power source, such as a battery. In some examples, the drain hub can include a mechanism to remove clogs that may be powered by the battery or the source of negative pressure. The mechanism to remove clogs can be disposed within the fluid pathway 48 or form at least part of the fluid pathway 48. The cartridge 40 can collect fluid drained from the patient as well as provide a source of negative pressure to draw fluid into the container 30. Sensors of the drain hub 42 may detect parameters of the fluid from outside of the cartridge 40 or outside the surfaces of the cartridge 40 and not contact the fluid.

Figure 3:
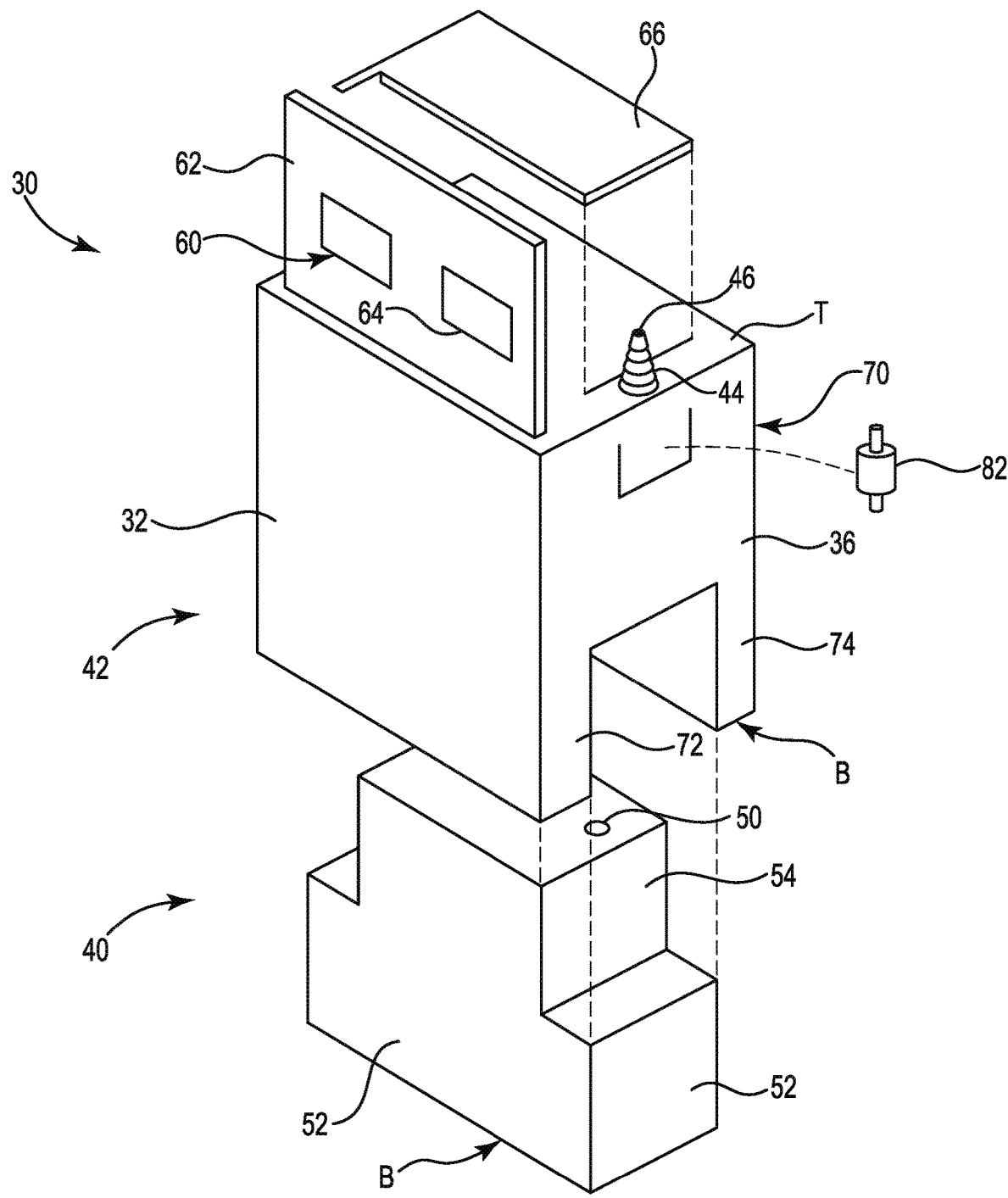
FIG. 3 is an exploded view of the container of FIG. 2.

FIG. 3 illustrates an exploded view of the portable container 30. In one example, the cartridge 40 is removably coupled to the drain hub 42 via clips or other releasable fastener mechanisms, such as on the insides of the major surfaces 32, 34. For example, a user may squeeze the drain hub 42 or pull the cartridge 40 away from the drain hub 42 in such as way as to release the cartridge 40. The cartridge 40, when released from the drain hub 42, may be emptied and returned to the drain hub 42 to receive additional fluid or replaced with a new cartridge to receive additional fluid. In one example, the cartridge 40 includes an opening 50 and a set of walls 52 surrounding a vessel 54 configured to receive the fluid. When the cartridge 40 is installed in the drain hub 42, the opening 50 is configured to be in fluid communication with the fluid port 46 and fluid pathway 48 to receive fluid into the vessel 54. The cartridge 40 can include translucent, including transparent, walls 52 or include a translucent or transparent section of one or more walls 52 to allow sensors on the container 30 such as drain hub 42 to detect features of the fluid in the vessel 54, such as color of the fluid or volume of the fluid. In one example, the entire vessel 54 is constructed from a translucent material.

In one example of an active drain system 10, the vessel 54 can be provided with a prescribed vacuity such as a pressure less than ambient pressure, and is sealed at the prescribed pressure prior to installation into the drain hub 42. For example, the walls 52 are generally rigid, as opposed to pliable and collapsible under the negative pressure, and a prescribed vacuity is preset at a factory or otherwise by sealing the opening 50 with a cover. The drain hub 42 can be provided with a mechanism or article, such as on the fluid pathway 48, to pierce the cover of the opening 50 when the cartridge 40 is installed into the drain hub 42. The fluid pathway 48 can include components such as O-rings or other features to help seal the fluid connection between the fluid pathway 48 and the cartridge 40. A differential pressure is created between the surgical or wound site 14 and the vessel 54 to draw fluid from the wound site 14 into the vessel 54. In one example, the particular cartridge 40 selected for attachment to the drain hub 42 can be chosen based on the vacuity of the cartridge 40 appropriate for the application. Cartridges may be manufactured with selected vacuities, and some vacuities may be preferred for some applications. Once the cartridge 40 is installed into the drain hub 42 such that a fluid connection is made with the opening 50 and the fluid pathway 48, the container 30 provides a source of negative pressure to begin to draw fluid into a drain, such as drain 16. In some examples, the opening 50 can include a one-way valve to prevent spillage when a cartridge 40 is removed from the drain hub 42.

The cartridge 40 including the vessel 54 provided with the prescribed vacuity provides several advantages over other drain systems. As compared to Jackson-Pratt drains, the vessel is preloaded to the appropriate vacuity and the patient or clinician does not manually attempt to set or create the vacuum in the bulb. Further, manually creating a vacuum on a Jackson-Pratt drain after it has been emptied of fluid can be messy, which is avoided with a new cartridge 40. Also, the present drain system 10 avoids the bulk, weight, noise, heat, and high power requirements of mechanical pump-based systems, such as peristaltic pumps. Drain systems with peristaltic pumps may include additional insulation to protect the patient from heat or noise of the pump and either include large batteries to power the pump or include frequent electrical coupling to an external power source to recharge the drain system, which includes added circuitry and size.

FIG. 3 also illustrates the drain hub 42 includes circuit components 60, such as a printed circuit board 62 having a one or more circuit elements and electrical pathways to operably couple the circuit elements to one or more sensors 64 located on the drain hub 42. The circuit components 60 may be arranged on one or more printed circuit boards, such as circuit board 62. In one example, circuit components 60 include a processing circuit and a communications module including one or more integrated circuits described in greater detail below. The drain hub 42 can also be configured to receive a power source 66, such as rechargeable battery or a removable battery, to provide electrical power to at least the circuit elements. The drain hub 42 can include buttons, membrane switches, or other user interface mechanisms (not shown) operably coupled to the circuit components 60 to the to allow a user to control aspects of the drain system 10. The drain hub 42 can also include lights, such as light emitting diodes, or other alert mechanisms (not shown) to provide alerts or notifications to the user regarding the status of the drain system 10. Buttons and lights can be provided on one or more of the surfaces B, T, 32, 34, 36, 38.

In the illustrated example, the drain hub 42 can include a top receiver 70 proximate the top surface T including the drain connection 44, a first side 72 or first wall and a second side 74 or second wall. First and second sides 72, 74 can form major surfaces 32, 34. In the example, at least one of the first side 72 and second side 74 can be formed as hollow walls or walls having an internal structure to receive the printed circuit board 62 and one or more sensors within its interior. Power source 66 can be included in the top receiver 70. The cartridge 40 can be received in drain hub 42 between first and second sides 72, 74 and into top receiver 70. The sides 72, 74 and top receiver 70 can be formed from a rigid material to protect the circuit components 60 and power source 66 as well as to couple to the cartridge 40 such as at the rigid walls 52 of the cartridge 40.

Figure 4:
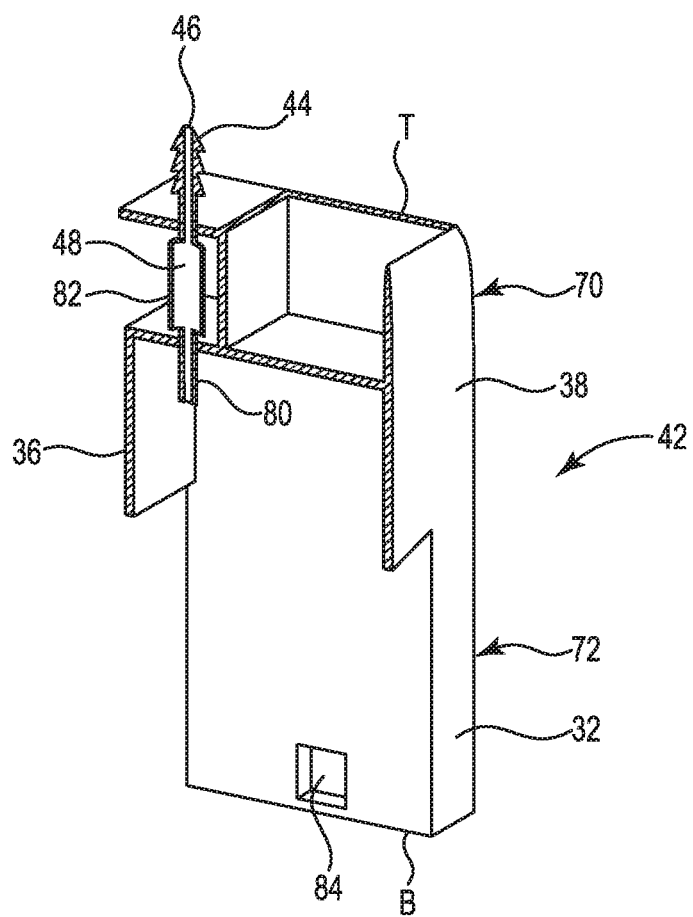
FIG. 4 is a perspective view of a section of an example drain hub of the example container of FIG. 2.

FIG. 4 illustrates a sectioned view of the drain hub 42 taken along lines 4-4 on FIG. 3. FIG. 4 provides a view of fluid pathway 48, which extends from drain connection 44 into a tube 80 that can be configured to pierce a seal in opening 50 and be in fluid communication with vessel 54 of cartridge 40. Fluid pathway 48 can include a turbine 82 that can spin to remove clogs in a fluid path between the drain 16, tubing 18, and fluid pathway 48. In the illustrated example, the turbine 82 can spin along an axis of the fluid pathway 48, although a turbine can be included to spin about another axis. The turbine 82 can be activated by the differential pressure between the vessel 54 and the drain site 14 or be separately powered and activated by circuit components 60.

In an indicated example, the turbine 82 can include an axially-extending hub or boss along the path of flow with a plurality of radially extending fins or blades. The example indicates the fins or blades extend along the side of the hub or boss along a generally straight line in the direction of the axis. Other configurations are contemplated. For example, the fins or blades can be coiled around the hub in a screw-like configuration. Additionally, the fins or blades can be in the shape of propeller blades. The turbine 82 can be disposed within a lumen forming a fluid pathway 48. The rotation of the turbine 82 can disrupt the fluid flow and loosen clogs or the rotation of the blades can generate a thrusting force in the fluid similar to a ship's propeller to dislodge clogs. In other examples, the hub or boss can be axially-extending walls of a hollow cylinder forming a lumen. The cylinder can be open at both ends, and the inner surface of the walls can include inwardly radially extending fins or blades. The fins or blades can extend along the axis in a straight line or be configured like an impeller or other similar device. Fluid can flow through the lumen formed by the hollow walls of the cylinder. In this example, the hollow cylinder can be disposed within the lumen of the forming the fluid pathway or the lumen formed by the hollow cylinder can form the fluid pathway 48.

At least one sensor window 84 can be included on the interior of a side 72, 74 of the drain hub facing the cartridge 40 and proximate the bottom surface B. A color sensor can be installed in the drain hub 42 proximate the sensor window 84 to detect color of the fluid in the vessel 54 through a translucent wall 52. The size and shape of the sensor window 84 is illustrated as an example, and other sizes or shapes are contemplated. The interior of a wall 72, 74 can include addition sensor windows to detect other features of the fluid such as volume.

Figure 5:
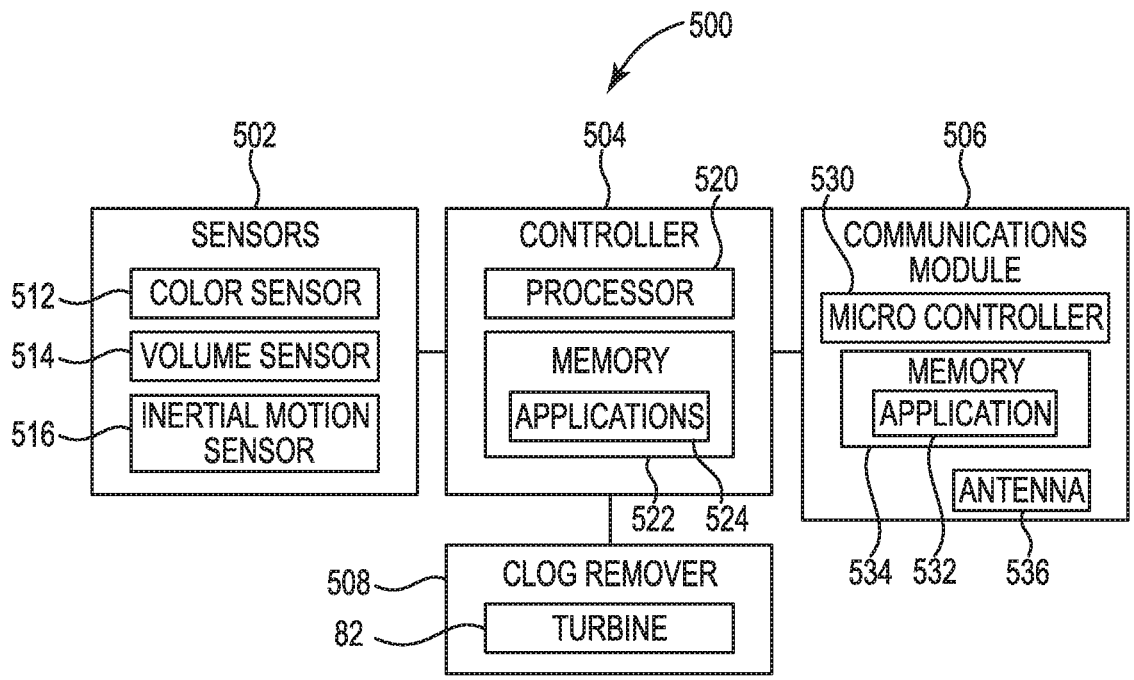
FIG. 5 is a schematic view of an example circuit board of the example container of FIG. 2.

FIG. 5 illustrates an example monitoring system 500, which may include an electronics module having one or more of the circuit elements 60 included on one or more circuit boards, such as the printed circuit board 62. Monitoring system 500 includes one or more sensors 502 coupled to a controller 504. The controller 504, in one example, is operably coupled to a communication module 506 to send and, in some examples, receive communications. Additionally, the controller 504 can be configured to selectively operate a clog remover 508 coupled to the turbine 82 to help remove clogs of fibrin, clots, or other materials that may build up in the drain lumen.

Sensors 502 can include one or more sensors such as a color sensor 512 to detect color of the fluid in the cartridge, volume sensor 514 to detect the volume of the fluid in the cartridge 40, and an inertial motion sensor 516 to determine the orientation of the container 30. For example, the printed circuit board 62 can include a nine-axis microelectromechanical system (MEMS) inertial motion sensor 516 that may include a three-axis gyroscope, three-axis accelerometer, and three-axis magnetometer to detect orientation of the container 30, which can be applied to determine whether to measure volume of fluid in the cartridge 40. If, for example, the cartridge 40 is upright or in a selected orientation, the controller 504 can selectively receive a signal from the volume sensor 514 to determine the amount of fluid in the cartridge 40. The controller 504 can selectively receive a signal from the color sensor 512 to determine whether the drainage fluid is clear, cloudy, yellowish, or includes blood.

In one example, the sensors 502 can also include a flow sensor to detect an amount of flow of fluid into the cartridge 40. In other examples, an amount of flow can be detected inferentially with one or more other sensors, such as the volume sensor 514. For instance, the controller 504 can determine an amount of flow from a volume $v_0$ measured at a time $t_0$ and a volume $v_1$ measured at a subsequent time $t_1$. An amount of flow F of the fluid into the cartridge 40 can thus be calculated from $F=(v_1-v_0)/(t_1-t_0)$. Still further, the sensors 502 can include a temperature sensor, such as a thermocouple, to detect whether the patient is running a fever and other sensors.

In some examples, one or more sensors 502 can be located on the drain system and remote from the container 30. For example, the thermocouple can be located on the drain 16 or tubing 18, which is embedded in the patient at the surgical site, and coupled to the controller via signal pathways such as wires or traces.

Controller 504 can include circuitry to receive and process signals from the sensors 502, provide output signals to the communications module 506 and clog remover 508, and receive and process signals from communication module 506. In one example, controller 504 can include a processor 520 and memory 522 as well as various analog-to-digital converters or digital-to-analog converters are applied to provide and receive signals to various components. Processor 520 can include a microcontroller for one or more embedded applications 524 in memory 522, such as a small computing device on a single integrated circuit including one or more processor cores, memory, and programmable input/output peripherals. Memory 522 can include nonvolatile or programmable memory, such as flash memory and one-time programmable read only memory (ROM), can be provided to include, for example, computer implemented instructions for controlling the processor 520, is also often included on a chip, as well as a typically small amount of volatile memory such as random access memory (RAM), to include, for example, computer implemented instructions and computer readable data for controlling the processor 520.

Processing of signals can be implemented in a combination of hardware and computer programming in controller 504. For example, the programming can be processor-executable instructions stored on at least one non-transitory machine-readable storage medium, such the memory 522. The hardware can include at least one processor 520 to execute the instructions 524 loaded or stored in memory 522. In some examples, the hardware can also include other electronic circuitry to at least partially implement at least one feature of the processing.

Controller 504 can determine, based on signals received from the volume sensor 514, whether there is enough fluid to process signals from the color sensor 512. Further, controller 504 can determine, based on signals from the inertial motion sensor 516, whether the container 30 is upright or selectively oriented to receive signals from the volume sensor 514 and the color sensor 512. Still further, the controller 504 can determine time of measurement to determine flow based on two or more volume measurements. Additionally, the controller 504 can determine based on flow measurements over time whether a clog may be present or whether the wound or surgical site 14 has stopped draining fluid.

If, for example, the controller 504 determines a clog is present in the container, the controller 504 may automatically provide a signal to the clog remover 508 to operate the turbine 82 and remove the clog. Alternatively, or additionally, the controller 504 may provide a notification to the patient, caregiver, or a remote care center alerting the presence of a clog.

The communication module 506 can be configured to include a wireless-network connectivity microcontroller 530 for an embedded application 532 stored in memory 534, such as a small computing device on a single integrated circuit including a processor core, memory, and programmable input/output peripherals. Nonvolatile or programmable memory, such as flash memory and ROM, to include, for example, computer implemented instructions for controlling the module, is also often included on the chip, as well as a typically small amount of volatile memory such as additional RAM), to include, for example, computer implemented instructions and computer readable data for controlling the module. Optional features of the module can include input/output serial ports, such as universal asynchronous receiver/transmitter (UART) or other serial communication interfaces such as inter-integrated circuits (I2C). The communications module can include one or more network processors subsystems for network-on-a-chip having a dedicated processor and memory for radio, baseband, and media access control (MAC) with encryption features as well as embedded internet protocol suite (TCP/IP) and cryptographic protocols (TLS/SSL) stacks, hypertext transfer protocol (HTTP) server, and other network protocols. Additionally, the communications module 506 can include a wireless-network antenna 536.

In one particular example of the monitoring system 500, the controller 504 can periodically or intermittently determine whether to receive signals from the some of the sensors 502, particularly the color sensor 512 and volume sensor 514. For example, the controller can determine from signals provided the inertial motion sensor 516 whether measurements from the volume sensor 514 would be accurate and whether fluid is proximate the color sensor 512. If not, the controller 504 could reschedule measurements or wait until the next scheduled measurement to receive signals. If so, the controller 504 could receive measurements from the volume sensor 514 and the color sensor 512.

One aspect of the volume measurement could be used to determine if the fluid has reached its volume limit within the cartridge 40. If so, the controller 504 could provide a message via communication system 506, via an indicator light or sound, or other notification, to the patient or caregiver to replace the full cartridge with a new and empty cartridge. The controller 504 can also be configured to detect the presence of the new and empty cartridge, via a volume measurement or other mechanism, and restart or reset the process of periodically or intermittently receiving signals from the sensors 502.

Similarly, a notification can be provided if signals received from the color sensor 512 are determined to be outside of parameters for a given time or changes in the color signal over a period of time are determined to be outside of parameters. In some examples, parameters can be stored in memory and compared via processor on monitoring system 500. In other examples, sensor signals can be transmitted to a remote computing device that processes the signals against parameters and provides a notification.

Figure 6:
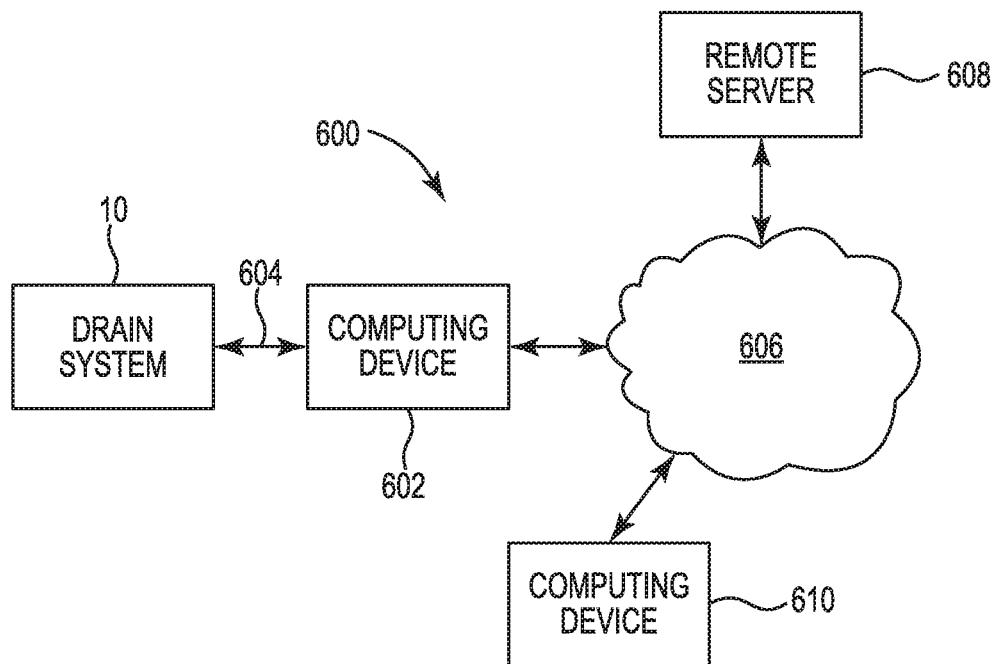
FIG. 6 is a schematic view of an example communication system including the example drain system of FIG. 1.

FIG. 6 illustrates an example communications system 600 for use with drain system 10. In the example, the communications module 506 of the drain system 10 can communicate directly with a computing device 602 over a wireless-network 604. The computing device 602 can be configured to exchange data from the drain system, or data processed from data from the drain system 10 via another communications network 606, e.g., a local area network or wide area network such as the Internet or other network, to a remote server 608. In one example, a computing device 610 can access the data related to the drain system 10 on the remote server 608 via an application over the communications network 606.

In one example, the communications module 506 of the container 30 can exchange computer data with computing device 602, which can include a mobile device, laptop, or network intermediary, via a wireless technology suitable for short distances. The computing device 602 can then exchange the computing data or additional processed data, over the communications network 606 to the remote server 608, which, in one example, is located in a data center. A clinician, the patient or caregiver can access the remote server via computing device 610, which can include a laptop, desktop, workstation, mobile device or other, or in some examples, via computing device 602.

The computing device 602 can include a general purpose mobile device such as a smartphone or tablet, laptop, or other computing device, or special purpose medical device configured to exchange data with the drain system 10. In this example, the computing device 602 can be provided with a computer program configured to relay data from the drain system 10 to the remote server 608 such as information processed from the sensors and, in some examples, receive information from the remote server and provide the information to the communications module 506, such as firmware updates. Additionally, the computer program can be configured to present data from the communications module in form usable by the patient or caregiver, such as a user interface that can alert the patient or caregiver to change the cartridge or other information. Also, the user interface can allow the patient or caregiver to interact with the drain system, such as controls that can operate the clog remover 508. Still further, the user interface can be configured to present information from the remote server.

Examples of wireless-networks 604 for use with the drain system 10 include wireless local area network (WLAN), wireless personal area networks (WPAN), wireless body area networks (WBAN) or other wireless networks for exchanging computer data over relatively short distances. In one example WLAN includes a wireless distribution method such as spread-spectrum or orthogonal frequency-division multiplexing (OFDM) radio within a limited area such as a home, school, office, or care center. Example WLANs include IEEE 802.11, which is a set of media access control (MAC) and physical layer (PHY) specifications for implementing WLAN computer communication in the 900 MHz and 2.4, 3.6, 5, and 60 GHz frequency bands created and maintained by the Institute of Electrical and Electronics Engineers (IEEE) LAN/MAN Standards Committee (IEEE 802). The communication standards and amendments can be implemented in products available under the trade designation Wi-Fi. One example WPAN exchanges data over short distances using short-wavelength ultra-high frequency radio waves in the industrial, scientific, and medical (ISM) band from 2.4 to 2.485 GHz (2402 and 2480 MHz or 2400 and 2483.5 MHz) based on frequency-hopping spread spectrum technology. Example WPANs and WBANs include IEEE 802.15, which is a set of wireless specialty network standards and can include products available under the trade designation Bluetooth.

The communications module 506 can be configured to exchange data in the wireless-network 604 with computing device 602 in several configurations. For example, the communications module 506 can be configured to exchange data in the wireless-network 604 with the computing device 602 via a networking device intermediary such as a wireless router or gateway, a communications device available under the trade designation CareLink Monitor from the present assignee, or other networking device. The communications module 506 can be configured to exchange data in the wireless-network 604 directly with the computing device 602 such as in a peer-to-peer configuration. In some examples, the communications module 506 can be selectively configured to exchange data with a computing device 602 via a networking device intermediary and/or peer-to-peer.

In some examples, the computing device 602 can be replaced with a networking device intermediary such as the wireless router or gateway or the communications device available under the trade designation CareLink Monitor.

In one example, the computing device 610 can be provided with one or more computer programs of one or more computer programs, such as computer programs specifically configured for a patient or caregiver, computer programs specifically configured for clinicians, computer programs specifically configured for researchers, or other programs. In one example, computer programs can be configured to receive data such as information processed from the sensors. In another example, a computer program can be configured to receive telemetry data related to operation of the systems and applications of the drain system and not related to patient data. In one example, the computer program is a browser-based application. The computer program can be configured to present data from the communications module in form usable by the patient or caregiver or clinician, such as a user interface that can alert the patient or caregiver to change the cartridge 40 or other information that may present data differently or have addition functionality as a mobile application. Also, the user interface can allow the patient or caregiver to interact with the drain system 10, such as controls that can operate the clog remover 508.

Although the present disclosure has been described with reference to preferred embodiments, workers skilled in the art will recognize that changes can be made in form and detail without departing from the spirit and scope of the present disclosure.

What is claimed is:

1. A container for a portable surgical drain system to receive a fluid from a drain at a surgical site, the container comprising:
   a drain hub in fluid communication with the drain and having a side and at least one sensor, the side including a sensor window and the sensor being disposed proximate an interior of the side and the sensor window; and
   a pumpless cartridge removably coupled to the drain hub in fluid communication with the drain via the drain hub to draw, against an exterior of the side, and receive the fluid from the surgical site via a one-way valve in the pumpless cartridge;
   wherein the at least one sensor detects fluid color, fluid volume in the cartridge, and orientation of the container from outside of the cartridge, wherein the detection of fluid volume and fluid color are based on whether the container is detected in a selected orientation.

2. The container of claim 1 wherein the drain hub includes a processing circuit configured to receive signals from the at least one sensor.

3. The container of claim 2 wherein the drain hub includes a communications module operably couplable to a computing device via a wireless-network to exchange computer data between the processing circuit and the computing device.

4. The container of claim 2 wherein the at least one sensor includes a plurality of sensors including an inertial motion sensor and a volume sensor.

5. The container of claim 4 wherein the processing circuit is configured to receive a signal from the volume sensor when the container is in a selected orientation as determined from a signal from the inertial motion sensor.

6. The container of claim 5 wherein the processing circuit is configured to provide an alert when the cartridge is full of fluid.

7. The container of claim 6 wherein the cartridge is set at a prescribed pressure.

8. The container of claim 1 wherein the drain hub includes a fluid pathway configured to be in fluid communication with the drain and the cartridge, wherein the fluid pathway includes a turbine configured to be rotated about an axis within the fluid pathway.

9. A container for a portable surgical drain system to receive a fluid from a drain at a surgical site, the container comprising:
   a drain hub having a top surface with a fluid port, a bottom surface, and a side surface of a plurality of side surfaces, the side surface having a sensor window, wherein the top surface, bottom surface and plurality of side surfaces defining an interior having at least one sensor proximate the sensor window; and
   a generally rigid cartridge removably coupled to the drain hub in fluid communication with the drain to draw and receive the fluid from the surgical site, the generally rigid cartridge having a prescribed vacuity when installed into the drain hub proximate an exterior of the side surface, the generally rigid cartridge contained within the top surface, plurality of side surfaces, and bottom surface of the drain hub;
   wherein the at least one sensor detects characteristics of the fluid in the cartridge without contacting the fluid, the detected characteristics including fluid volume and fluid color, wherein the detection of fluid volume and fluid color are based on whether the drain hub is detected in a selected orientation.

10. The container of claim 9 wherein the cartridge includes a cover and the drain hub includes an article to pierce the cover when the cartridge is installed into the drain hub.

11. The container of claim 10 wherein drain hub is in fluid communication with the drain.

12. The container of claim 11 wherein the cartridge provides a source of negative pressure for the drain system when installed into the drain hub.

13. The container of claim 9 wherein the cartridge includes a cover that is pierced by the drain hub when the cartridge is installed into the drain hub, the cover provided over an opening that is in fluid communication with the drain when the cartridge is installed into the drain hub.

14. The portable surgical drain system of claim 9 wherein the at least one sensor includes an inertial motion sensor to detect orientation of the container.

15. The portable surgical drain system of claim 9 including a processing circuit configured to receive signals from the at least one sensor.

16. A container for a portable surgical drain system to receive a fluid from a drain at a surgical site, the container comprising:
   a drain hub having a plurality of walls defining an exterior, the drain hub having at least one sensor being disposed within the plurality of walls; and
   a generally rigid cartridge removably coupled to and against the drain hub in fluid communication with the drain to provide a suction source to draw and receive the fluid from the surgical site, the generally rigid cartridge contained within the walls defining the exterior of the drain hub;
   wherein the at least one sensor detects a characteristic of the fluid in the container from outside of the cartridge, the detected characteristics including fluid color, wherein the detection of fluid color is based on whether the drain hub is detected in a selected orientation.

17. The container of claim 16 wherein the characteristic that the at least one sensor detects includes at least one of fluid color, fluid volume in the cartridge, and orientation of the container.

18. The container of claim 16 wherein the suction source is a negative pressure.

19. The container of claim 18 wherein the suction source is a prescribed vacuity in the cartridge.

20. The container of claim 16 wherein the at least one sensor includes a volume sensor to detect fluid volume in the cartridge.

21. A portable container for a surgical drain system to receive a fluid from a drain at a surgical site, the portable container comprising:

a drain hub having a plurality of sides defining an interior, the drain hub in fluid communication with the drain; and a cartridge removably coupled to the drain hub in fluid communication with the drain to receive the fluid from the surgical site;

wherein the drain hub includes at least one sensor configured to fluid color, fluid volume in the cartridge, and orientation of the container from the interior of the drain hub and outside of the cartridge without contacting the fluid, wherein the detection of fluid color is based on whether the drain hub is detected in a selected orientation; and wherein the interior of the drain hub includes a fluid pathway configured to be in fluid communication with the drain and the cartridge, wherein the fluid pathway includes a turbine configured to be rotated about an axis within the fluid pathway, the turbine activated by differential pressure between the cartridge and the surgical site.

22. The portable container of claim 21 wherein the drain hub includes a processing circuit configured to receive signals from the at least one sensor.

23. The portable container of claim 22 wherein the drain hub includes a communications module operably couplable to computing device via a wireless-network to exchange computer data between the processing circuit and the computing device.

24. The portable container of claim 22 wherein the at least one sensor includes a plurality of sensors including an inertial motion sensor and a volume sensor.

25. The portable container of claim 24 wherein the processing circuit is configured to receive a signal from the volume sensor when the container is in a selected orientation as determined from a signal from the inertial motion sensor.

26. The portable container of claim 25 wherein the processing circuit is configured to provide an alert when the cartridge is full of fluid.

27. The portable container of claim 21 wherein the cartridge is set at a prescribed pressure.

28. A container for a portable surgical drain system to receive a fluid from a drain at a surgical site, the container comprising:
a drain hub having a translucent window and at least one sensor disposed in the translucent window and an axial fluid pathway configured to be in fluid communication with the drain, the fluid pathway including a turbine configured to be rotated about an axis of rotation within the fluid pathway; and a generally rigid cartridge removably coupled to the drain hub in fluid communication with the drain to draw and receive the fluid from the surgical site via the fluid pathway, the generally rigid cartridge having a prescribed vacuity when installed into the drain hub;

wherein the at least one sensor detects a characteristic of the fluid in the cartridge from outside of the cartridge through the translucent window without contacting the fluid, the detected characteristic including fluid color, wherein the detection of fluid color is based on whether the drain hub is detected in a selected orientation, and the turbine is rotated by a force from the prescribed vacuity of the cartridge, and wherein the turbine is activated by differential pressure between the cartridge and the surgical site.

29. The container of claim 28 comprising a processing circuit operably coupled to the at least one sensor and configured to receive a signal from the at least one sensor wherein the processing circuit is configured to selectively provide a notification if a clog is determined in the drain system.

30. The container of claim 28 wherein the turbine is configured as a hub having an axis corresponding with the axis of rotation of a plurality of fins radially extending from the hub.

31. The container of claim 30 wherein the turbine is disposed within a lumen of the fluid pathway.

32. A portable container for a surgical drain system to receive a fluid from a drain at surgical site of the surgical drain system, the portable container comprising:
a cartridge to draw and receive the fluid; and a drain hub, the cartridge removably coupled to the drain hub, the drain hub including a fluid pathway in fluid communication with the cartridge and the drain, the drain hub comprising:
a sensor configured to detect fluid color via a translucent window and without contacting the fluid in the cartridge, wherein the detection of fluid color is based on whether the drain hub is detected in a selected orientation;

a processing circuit operably coupled to the sensor and configured to receive signals from the sensor;

a communications module operably coupled to the processing circuit to transmit computer data received from the processing circuit to a computing device on over a wireless-network; and a turbine disposed within the fluid pathway and operably coupled to the processing circuit wherein the processing circuit is configured to selectively operate the turbine if a clog is determined in the drain system, the turbine including coiled blades coupled to a rotating hub to generate a thrusting force in the fluid pathway.

33. The portable container of claim 32 wherein the computing device is one of a mobile device and a network intermediary.

34. The portable container of claim 33 wherein the computing device is operably coupled to a remote server and the processing circuit is configured to exchange computer data with the remote server via the communications module.

35. The portable container of claim 33 wherein the mobile device is a smartphone.

36. The portable container of claim 32 wherein the sensor is configured to inferentially detect fluid flow.

37. The portable container of claim 36 wherein fluid flow is determined via change in fluid volume over a period of time.

38. The portable container of claim 32 wherein the cartridge is generally rigid and includes a prescribed vacuity when installed into the drain hub.

39. A container for a portable surgical drain system to receive a fluid from a drain at a surgical site, the container comprising:
a drain hub having a plurality of walls and a sensor being disposed within the plurality of walls;

a cartridge removably coupled to the drain hub in fluid communication with the drain to provide a suction source to draw and receive the fluid from the surgical site, the cartridge having an exterior wall disposed against the drain hub at a wall of the plurality of walls; and a turbine including coiled blades coupled to a rotating hub, the turbine disposed in the drain hub to generate a thrusting force in a fluid pathway between the drain hub and the cartridge wherein the turbine is activated by differential pressure between the cartridge and the surgical site;

wherein the sensor detects a characteristic of the fluid in the container without contacting the fluid, and the cartridge is received within the walls of the drain hub, the detected characteristic including fluid color, wherein the detection of fluid color is based on whether the drain hub is detected in a selected orientation.

40. The container of claim 39 wherein the cartridge includes generally rigid walls and the suction source is a negative pressure.

41. The container of claim 40 wherein the negative pressure is a prescribed vacuity.

42. The container of claim 39 wherein the sensor is disposed within a wall of the plurality of walls of the drain hub.

43. The container of claim 42 wherein the wall of the plurality of walls includes a translucent window proximate the sensor.

44. The container of claim 43 wherein the cartridge includes generally translucent walls proximate the translucent window.

45. The container of claim 44 wherein the translucent window and translucent walls of the cartridge are generally transparent.

46. The container of claim 42 wherein the drain hub includes a processing circuit operably coupled to the sensor and configured to receive signals from the sensor, wherein the processing circuit is disposed within the wall of the drain hub.

47. The container of claim 46 wherein the drain hub includes a communications module operably coupled to the processing circuit to transmit computer data received from the processing circuit, wherein the communication module is disposed with the wall of the drain hub.

48. The container of claim 46 wherein the drain hub includes a plurality of sensors configured to detect fluid color, fluid volume in the cartridge, and orientation of the container, the plurality of sensors coupled to the processing circuit.

49. The container of claim 39 wherein the cartridge is received entirely within the walls of the drain hub.

50. The container of claim 39 wherein the characteristic of the fluid futher includes fluid volume.

51. A container for a portable surgical drain system to receive a fluid from a drain at a surgical site, the container comprising:

a drain hub having a top receiver and a plurality of sides defining an interior, wherein the top receiver includes a drain connection and a fluid pathway configured to be in fluid communication with the drain, and wherein at least one of the plurality of sides includes a sensor window and a sensor within the interior proximate the sensor window; and a cartridge removably coupled to the drain hub in fluid communication with the drain to provide a suction source to draw and receive the fluid from the surgical site, the cartridge disposed against the at least one side, the cartridge contained within the walls defining the interior of the drain hub; and a turbine disposed in the drain hub to generate a thrusting force in the fluid pathway wherein the turbine is activated by differential pressure between the cartridge and the surgical site;

wherein the sensor detects a characteristic of the fluid in the container from outside of the cartridge, and the cartridge is received within the walls of the drain hub, the detected characteristic including fluid color, wherein the detection of fluid color is based on whether the drain hub is detected in a selected orientation.

52. The container of claim 51 wherein the fluid pathway includes lumen, and the turbine is disposed within the lumen.

53. The container of claim 51 wherein at least one of the plurality of sides includes a processing circuit operably coupled to the sensor and configured to receive signals from the sensor, and the top receiver includes a power source operably coupled to the processing circuit.

54. The container of claim 51 wherein the plurality of sides are generally rigid and include a translucent window proximate the sensor.

55. The container of claim 54 wherein the cartridge includes a plurality of translucent walls.

56. The container of claim 55 wherein the plurality of walls are generally rigid.

* * * * *